US012115063B2

(12) United States Patent
Bruchman et al.

(10) Patent No.: US 12,115,063 B2
(45) Date of Patent: Oct. 15, 2024

(54) MULTI-FRAME PROSTHETIC VALVE APPARATUS AND METHODS

(71) Applicant: Edwards Lifesciences Corporation, Irvine, CA (US)

(72) Inventors: William C. Bruchman, Camp Verde, AZ (US); Cody L. Hartman, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1300 days.

(21) Appl. No.: 16/402,967

(22) Filed: May 3, 2019

(65) Prior Publication Data

US 2019/0254815 A1 Aug. 22, 2019

Related U.S. Application Data

(63) Continuation of application No. 13/797,526, filed on Mar. 12, 2013, now Pat. No. 10,376,360.

(60) Provisional application No. 61/676,812, filed on Jul. 27, 2012.

(51) Int. Cl.
*A61F 2/24* (2006.01)

(52) U.S. Cl.
CPC .......... *A61F 2/2415* (2013.01); *A61F 2/2418* (2013.01); *A61F 2210/0076* (2013.01); *A61F 2220/005* (2013.01); *A61F 2230/0054* (2013.01)

(58) Field of Classification Search
CPC .................. A61F 2/2415; A61F 2/2418; A61F 2210/0076; A61F 2220/005; A61F 2220/0075; A61F 2230/0054; A61F 2/24; A61F 2220/0005; A61F 2230/054; A61L 27/14; A61L 31/022
See application file for complete search history.

(56) References Cited

U.S. PATENT DOCUMENTS

| 654,799 A | 7/1900 | Levett |
| 3,739,402 A | 6/1973 | Kahn et al. |
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |

(Continued)

FOREIGN PATENT DOCUMENTS

| AU | 2013363172 A1 | 7/2015 |
| AU | 2017202405 A1 | 4/2017 |

(Continued)

OTHER PUBLICATIONS

International Preliminary Report on Patentability received for PCT Patent Application No. PCT/US14/68727, mailed on Jun. 16, 2016, 9 pages.

(Continued)

*Primary Examiner* — Matthew W Schall
(74) *Attorney, Agent, or Firm* — Thomas C. Richardson

(57) ABSTRACT

Described embodiments are directed toward centrally-opening leaflet prosthetic valve devices having a leaflet frame coaxially disposed within a body frame, as well as methods of making the valve devices.

20 Claims, 10 Drawing Sheets

(56) References Cited

U.S. PATENT DOCUMENTS

| | | |
|---|---|---|
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St. Germain et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin, Jr. et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |

(56) References Cited

U.S. PATENT DOCUMENTS

| | | |
|---|---|---|
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287719 A1* | 12/2006 | Rowe .............. A61F 2/2409 623/2.18 |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |

(56) References Cited

U.S. PATENT DOCUMENTS

| | | |
|---|---|---|
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0005863 A1 * | 1/2009 | Goetz ............... A61F 2/2418 623/2.18 |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |

(56) References Cited

U.S. PATENT DOCUMENTS

| | | |
|---|---|---|
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De Cicco et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Lim et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 B1 | 6/2003 |
| EP | 1666003 A1 | 6/2006 |
| EP | 1395205 B1 | 7/2008 |
| EP | 1235537 B1 | 12/2008 |

(56) References Cited

FOREIGN PATENT DOCUMENTS

| | | |
|---|---|---|
| EP | 2193762 A1 | 6/2010 |
| EP | 2255750 A2 | 12/2010 |
| EP | 2359774 B1 | 8/2011 |
| EP | 2400923 A1 | 1/2012 |
| EP | 2489331 A2 | 8/2012 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| JP | 44-032400 | 12/1969 |
| JP | 196932400 B | 12/1969 |
| JP | 02-000645 A | 1/1990 |
| JP | 09-241412 A | 9/1997 |
| JP | 10507097 A | 7/1998 |
| JP | 11-290448 A | 10/1999 |
| JP | 11-512635 A | 11/1999 |
| JP | 2000511459 A | 9/2000 |
| JP | 2000513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010517623 A | 5/2010 |
| JP | 2010-528761 A | 8/2010 |
| JP | 2010-188189 A | 9/2010 |
| JP | 2010-535075 A | 11/2010 |
| JP | 2010536527 A | 12/2010 |
| JP | 2012504031 A | 2/2012 |
| JP | 2012152563 A | 8/2012 |
| JP | 2013-506439 A | 2/2013 |
| JP | 2013-543399 A | 12/2013 |
| JP | 2014-513585 A | 6/2014 |
| JP | 2014517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 1996002212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 0018333 A1 | 4/2000 |
| WO | 00/41649 A1 | 7/2000 |
| WO | 00/47271 A1 | 8/2000 |
| WO | 2000062716 A1 | 10/2000 |
| WO | 0128453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 2002024118 A1 | 3/2002 |
| WO | 2002024119 A1 | 3/2002 |
| WO | 02/47468 A1 | 6/2002 |
| WO | 2002045933 A2 | 6/2002 |
| WO | 02/60506 A1 | 8/2002 |
| WO | 2002100301 A1 | 12/2002 |
| WO | 03/03946 A1 | 1/2003 |
| WO | 2003007795 A2 | 1/2003 |
| WO | 2003047468 A1 | 6/2003 |
| WO | 03090834 A2 | 11/2003 |
| WO | 2004/000375 A1 | 12/2003 |
| WO | 2005/084595 A1 | 9/2005 |
| WO | 2005112827 A2 | 12/2005 |
| WO | 2006/019626 A2 | 2/2006 |
| WO | 2006/058322 A2 | 6/2006 |
| WO | 2006108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008097589 A1 | 8/2008 |
| WO | 2008097592 A2 | 8/2008 |
| WO | 2008/150529 A1 | 12/2008 |
| WO | 2009/017827 A1 | 2/2009 |
| WO | 2009029199 A1 | 3/2009 |
| WO | 2009045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010037141 A1 | 4/2010 |
| WO | 2010/086460 A1 | 8/2010 |
| WO | 2010/132707 A1 | 11/2010 |
| WO | 2010/150208 A2 | 12/2010 |
| WO | 2010057262 A8 | 6/2011 |
| WO | 2011/098565 A1 | 8/2011 |
| WO | 2011109450 A2 | 9/2011 |
| WO | 2011109801 A2 | 9/2011 |
| WO | 2011112706 A2 | 9/2011 |
| WO | 2012/004460 A2 | 1/2012 |
| WO | 2012/011261 A1 | 1/2012 |
| WO | 2012040643 A2 | 3/2012 |
| WO | 2012/047644 A2 | 4/2012 |
| WO | 2012065080 A2 | 5/2012 |
| WO | 2012082952 A2 | 6/2012 |
| WO | 2012/099979 A1 | 7/2012 |
| WO | 2012/116368 A2 | 8/2012 |
| WO | 2012110767 A2 | 8/2012 |
| WO | 2012135603 A2 | 10/2012 |
| WO | 2012/158944 A1 | 11/2012 |
| WO | 2012167131 A1 | 12/2012 |
| WO | 2013/074663 A2 | 5/2013 |
| WO | 2013/074990 A1 | 5/2013 |
| WO | 2013096854 A2 | 6/2013 |
| WO | 2013/109337 A1 | 7/2013 |
| WO | 2014/018189 A2 | 1/2014 |
| WO | 2014018432 A2 | 1/2014 |
| WO | 2014/099150 A1 | 6/2014 |
| WO | 2014099163 A1 | 6/2014 |
| WO | 2014099722 A1 | 6/2014 |
| WO | 2014/149319 A1 | 9/2014 |
| WO | 2014144937 A2 | 9/2014 |
| WO | 2014/181188 A2 | 11/2014 |
| WO | 2015/045002 A1 | 4/2015 |
| WO | 2015085138 A1 | 6/2015 |
| WO | 2015/171743 A2 | 11/2015 |
| WO | 2015/173794 A1 | 11/2015 |

(56) References Cited

FOREIGN PATENT DOCUMENTS

| WO | 2016028591 A1 | 2/2016 |
|---|---|---|
| WO | 2016044223 A1 | 3/2016 |
| WO | 2016100913 A1 | 6/2016 |
| WO | 2016/172349 A1 | 10/2016 |
| WO | 2016186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |
| WO | 2019/246268 A1 | 12/2019 |

OTHER PUBLICATIONS

International Search Report and Written Opinion for PCT/US2014/068727 dated Mar. 2, 2015, corresponding to U.S. Appl. No. 14/561,148; 6 pages.
International Search Report and Written Opinion received for PCT Patent Application No. PCT/US2018/050779, mailed on Dec. 7, 2018, 14 pages.
International Search Report for PCT/US2013/075274 mailed Feb. 27, 2014, corresponding to U.S. Appl. No. 13/843,196, t pages.
International Search Report and Written Opinion received for PCT Patent Application No. PCT/US15/50113, mailed on Nov. 24, 2015, 14 pages.
International Search Report and Written Opinion received for PCT Patent Application No. PCT/US2018/050769, mailed on Nov. 27, 2018, 11 pages.
Certified Copy of Priority Document for U.S. Appl. No. 61/739,721, received by the International Bureau Jan. 3, 2014, 1 page.
Certified Copy of the Application Data Sheet, Drawings, Specification, Claims, and Abstract filed under U.S. Appl. No. 13/843,196 on Mar. 15, 2013, 52 pages.
English translation of RU2434604 (C1), filed Apr. 30, 2010, translation powered by EPO and Google, 8 pages.
Opposition from EP17187595.8, filed Sep. 12, 2019, 50 pages.
Patent Assignment recorded on Aug. 9, 2014, under Patent Reel 033502 and Frame 0077, U.S. Appl. No. 14/133,563, 5 pages.
Patent Assignment recorded on May 23, 2013, under Patent Reel 030473 and Frame 0861, U.S. Appl. No. 13/843,196, 4 pages.
Clough, Norman E. Introducing a New Family of Gore ePTFE Fibers (2007), pp. 1-10.
European Search Report from EP16196687.4, mailed Nov. 21, 2017, 5 pages.
International Preliminary Report on Patentability from PCT/US2015/045002, mailed Mar. 2, 2017, 11 pages.
International Preliminary Report on Patentability issued in PCT/US2017/047174, mailed Mar. 7, 2019, 9 pages.
International Search Report and Written Opinion for PCT/US2014/068727 mailed Mar. 2, 2015, corresponding to U.S. Appl. No. 14/561,148; 12 pages.
International Search Report and Written Opinion for PCT/US2015/050113, mailed Nov. 24, 2015, 14 pages.
International Search Report and Written Opinion from PCT/US2018/050768, mailed Dec. 17, 2018, 12 pages.
International Search Report and Written Opinion from PCT/US2018/050786 mailed Dec. 14, 2018, 13 pages.
International Search Report and Written Opinion from PCT/US2018/053278, mailed Dec. 19, 2018, 12 pages.
International Search Report and Written Opinion issued in PCT/US2018/050764, mailed Nov. 23, 2018, 13 pages.
International Search Report and Written Opinion issued in PCT/US2018/050766, mailed Mar. 11, 2019, 16 pages.
International Search Report and Written Opinion issued in PCT/US2018/050778, mailed Nov. 29, 2018, 11 pages.
International Search Report for PCT/US2013/046389 mailed Jan. 21, 2014, corresponding to U.S. Appl. No. 13/797,633; 18 pages.
International Search Report for PCT/US2013/051431 mailed Jan. 20, 2014, corresponding to U.S. Appl. No. 13/797,526; 6 pages.
International Search Report for PCT/US2013/068390 mailed Apr. 29, 2014, corresponding to U.S. Appl. No. 13/835,988, 7 pages.
International Search Report for PCT/US2013/068780 mailed Feb. 27, 2014, corresponding to U.S. Appl. No. 13/869,878, 4 pages.
International Search Report for PCT/US2013/071632 mailed Apr. 28, 2014, corresponding to U.S. Appl. No. 13/841,334, 6 pages.
International Search Report for PCT/US2013/074962 mailed Feb. 27, 2014, 4 pages.
International Search Report for PCT/US2013/075274 mailed Feb. 27, 2014, corresponding to U.S. Appl. No. 13/843,196, 5 pages.
International Search Report for PCT/US2013/075380 mailed Mar. 6, 2014, 5 pages.
International Search Report for PCT/US2013/076504 mailed Apr. 28, 2014, corresponding to U.S. Appl. No. 14/133,491, 7 pages.
International Search Report for PCT/US2013/076688 mailed Feb. 27, 2014, 5 pages.
Cardiac Surgery in the Adult, Third Edition, Chapter 2 2008.
EPO Form 1002 for EP16196687.4 Filed Dec. 28, 2016.
European Search Report and Search Opinion Received for EP Application No. 18205790.1, mailed on Apr. 4, 2019, 7 pages.
European Search Report and Search Opinion Received for EP Application No. 15186981.5, mailed on Feb. 10, 2016, 5 pages.
European Search Report and Search Opinion Received for EP Application No. 17167842.8, mailed on Jun. 21, 2017, 5 pages.
European Search Report and Search Opinion Received for EP Application No. 17176507.6, mailed on Sep. 6, 2017, 5 pages.
European Search Report and Search Opinion Received for EP Application No. 17187595.8, mailed on Dec. 4, 2017, 5 pages.
European Search Report and Search Opinion Received for EP Application No. 17194473.9, mailed on Feb. 26, 2018, 9 pages.
Extended European Search Report issued in EP Application No. 18204192.1, issued May 29, 2019.
International Preliminary Report on Patentability received for PCT Patent Application No. PCT/US13/68390, mailed on Jul. 2, 2015, 12 pages.
International Preliminary Report on Patentability received for PCT Patent Application No. PCT/US13/71632, mailed on Jul. 2, 2015, 11 pages.
International Preliminary Report on Patentability received for PCT Patent Application No. PCT/US13/74962, mailed on Jul. 2, 2015, 9 pages.
International Preliminary Report on Patentability received for PCT Patent Application No. PCT/US13/75274, mailed on Jul. 2, 2015, 8 pages.
International Preliminary Report on Patentability received for PCT Patent Application No. PCT/US13/75380, mailed on Jul. 2, 2015, 7 pages.
International Preliminary Report on Patentability received for PCT Patent Application No. PCT/US13/76504, mailed on Jul. 2, 2015, 13 pages.
International Preliminary Report on Patentability received for PCT Patent Application No. PCT/US13/76688, mailed on Jul. 2, 2015, 12 pages.
International Preliminary Report on Patentability received for PCT Patent Application No. PCT/US2013/046389, mailed on Feb. 5, 2015, 13 pages.
International Preliminary Report on Patentability received for PCT Patent Application No. PCT/US2013/051431, mailed on Feb. 5, 2015, 9 pages.
International Search Report and Written Opinion received for PCT Patent Application No. PCT/US2015/045002, mailed on Dec. 17, 2015, 13 pages.
International Search Report for PCT/US2013/075275 dated Jun. 11, 2014, corresponding to U.S. Appl. No. 13/843,196, 5 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of Gore (Trademark) ePTFE Fibers (2007).
Opposition from EP16196687.4, mailed on Dec. 12, 2019, 38 pages.

(56) References Cited

OTHER PUBLICATIONS

Forward citations for E12 obtained from: https://scholar.google.com/scholar?cites=5981833429320176658&assdt=2005&sciodt=0,5&hl=en.

Google Image Search Results, "S-Shaped", accessed Nov. 1, 2013.

International Preliminary Report on Patentability received for PCT Patent Application No. PCT/US2020/027921, mailed on Oct. 21, 2021, 11 pages.

International Preliminary Report on Patentability received for PCT Patent Application No. PCT/US2020/044603, mailed on Feb. 10, 2022, 9 pages.

International Search Report and Written Opinion received for PCT Patent Application No. PCT/US2020/044603, mailed on Oct. 20, 2020, 12 pages.

International Search Report and Written Opinion received for PCT Patent Application No. PCT/US2020/027921, mailed on Jul. 24, 2020, 16 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.

\* cited by examiner

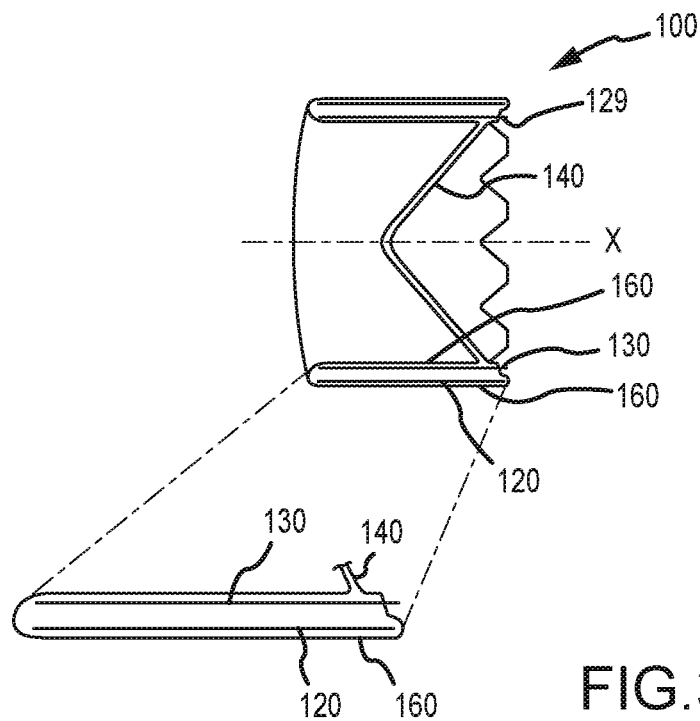
FIG.3A
FIG.3B
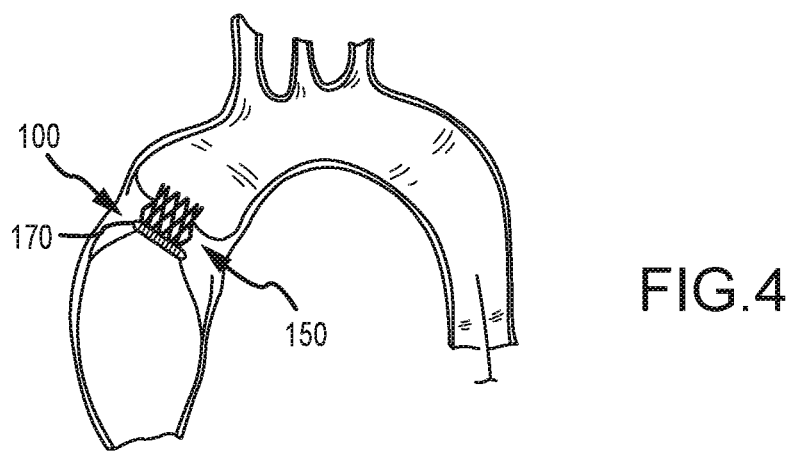
FIG.4

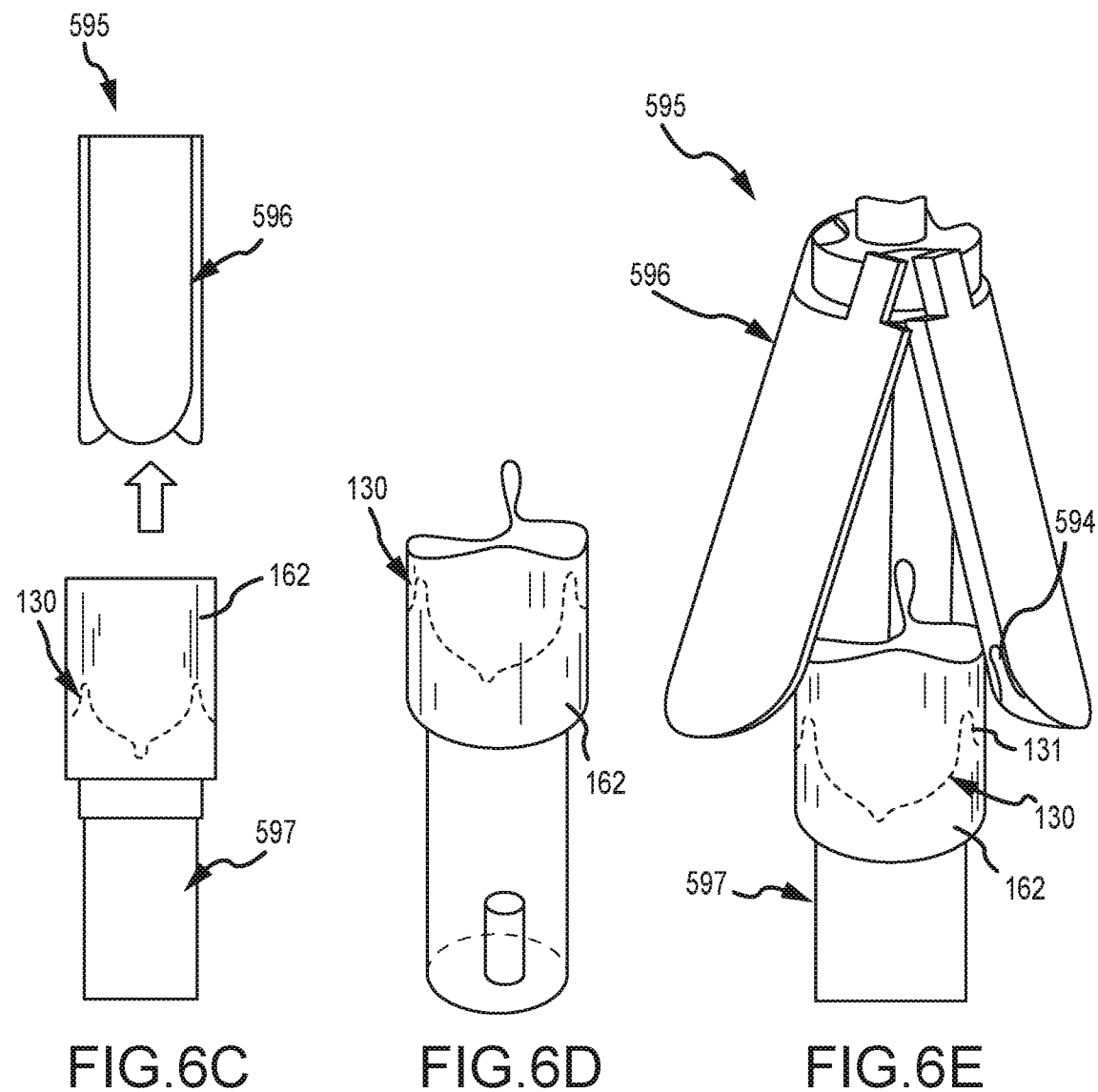

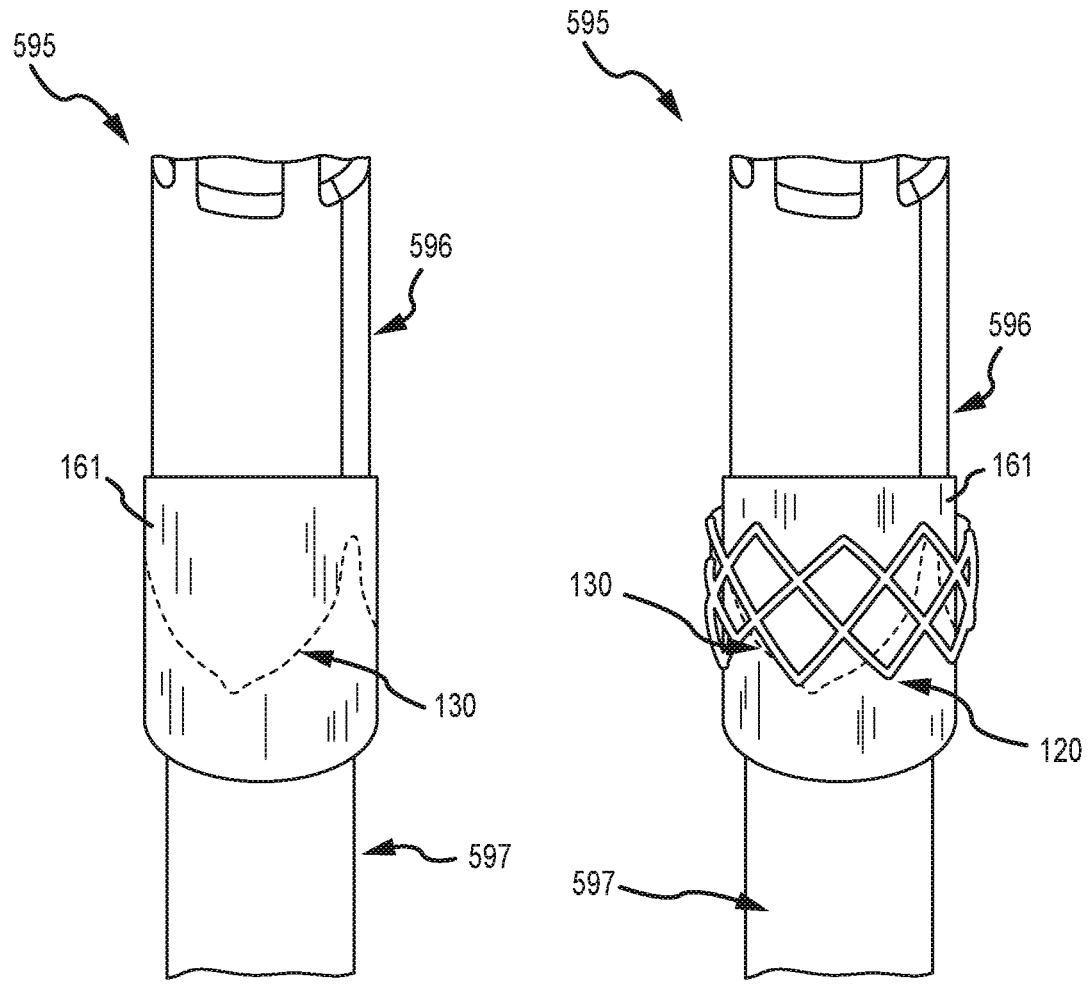

MULTI-FRAME PROSTHETIC VALVE APPARATUS AND METHODS

CROSS-REFERENCE TO RELATED APPLICATIONS

This application is a continuation of U.S. application Ser. No. 13/797,526, filed Mar. 12, 2013, which claims priority to provisional application Ser. No. 61/676,812 filed Jul. 27, 2012, both of which are herein incorporated by reference in their entireties.

FIELD

The present disclosure relates generally to prosthetic valves and more specifically synthetic flexible leaflet-type prosthetic valve devices, systems, and methods for implantation.

BACKGROUND

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

A number of fabrication techniques have been used to couple the leaflets to a frame, including sewing individual leaflets to the frame (biological and synthetic), and for synthetic leaflets only, injection molding and dip coating a polymer onto the frame. In many cases, the resulting leaflet is supported on the frame and defines a flap having a mounting edge where the leaflet is coupled to the frame and a free edge that allows the flap to move. The flap moves under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

There remains a need for a more durable flexible leaflet prosthetic valve.

SUMMARY

Described embodiments are directed to apparatus, system, and methods for valve replacement, such as cardiac valve replacement. More specifically, described embodiments are directed toward flexible leaflet valve devices having biological or synthetic leaflet material and a multi-part support member or frame, and methods of making and implanting the valve devices.

According to an embodiment, a valve comprises a leaflet frame, a body frame and any number of leaflets suitable for the size and function of the valve. According to another embodiment, a method of making the valve comprises the steps of fitting the leaflet frame and body frame with a biocompatible material as described herein, and thereby also forming leaflets.

According to an embodiment, a valve comprises a body frame defining a generally tubular shape defining a body frame lumen, a leaflet frame having a generally annular shape defining a plurality of U-shaped portions each defining a base and a plurality of posts, the leaflet frame being located coaxial with and at least substantially within the body frame lumen, a first film coupled to the body frame, and a second film coupled to and extending across each of the U-shaped portions defining a leaflet, each leaflet having a leaflet free edge, at least one of the first film and second film at least partially coupling the body frame to the leaflet frame, wherein the leaflet free edges are operable to abut adjacent leaflet free edges and are moveable between an open and closed position.

In accordance with a method of making a multi-frame prosthetic valve comprising: providing a body frame defining a generally tubular shape defining a body frame lumen; providing a leaflet frame having a generally annular shape defining a plurality of U-shaped portions each defining a base and a plurality of posts; providing a film; forming a first layer of the film into a tubular form; coaxially placing the leaflet frame over the tubular form of the first layer of film; wrapping the film around the leaflet frame and the tubular form of the first layer of film, the film extending across each of the U-shaped portions so as to define a leaflet therein; bonding the first layer and the second layer to each other and the leaflet frame; clamping the leaflets disposed in the U-shaped portions to enclose the leaflets; forming a third layer of the film over the leaflet frame; placing the body frame over the third layer of the film and over the leaflet frame such that the leaflet frame is coaxially disposed within the body frame lumen forming a fourth layer of the film over the body frame and the third layer of the film; and bonding the third layer and the fourth layer to each other and the body frame.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIGS. 3A and 3B are a side cross-sectional view and detail view, respectively, of an embodiment of a valve;

FIG. 4 is a side view of an embodiment of a valve within anatomy in accordance with an embodiment;

FIGS. 6A-6H are various side and perspective views of an embodiment of assembling a valve.

DETAILED DESCRIPTION

Figure 1A:
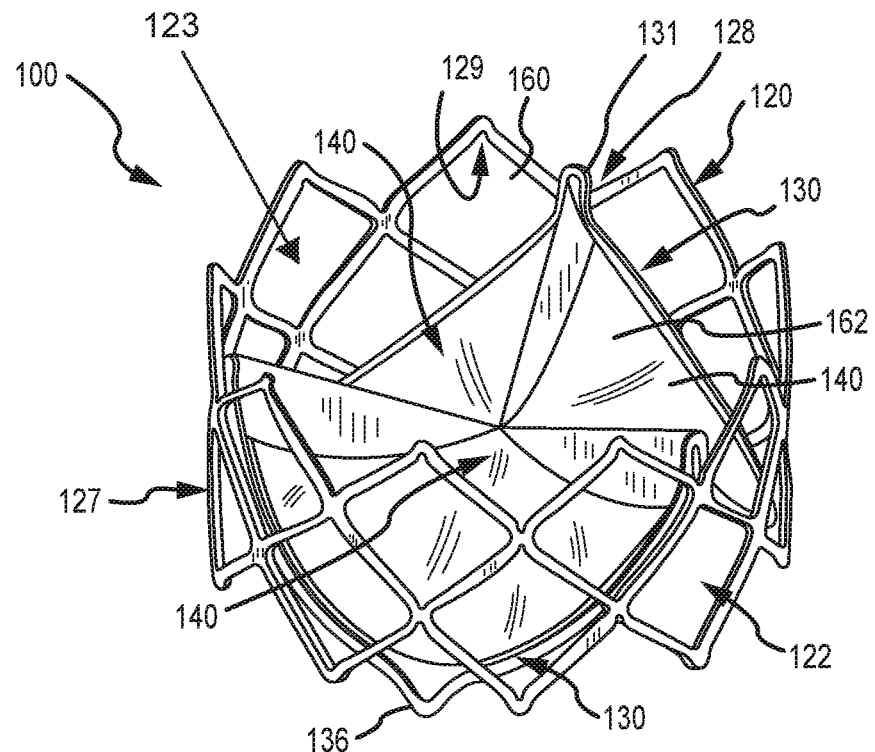
FIG. 1A is a perspective view of an embodiment of a valve comprising a leaflet frame and a body frame.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a flexible component of a one-way valve wherein the leaflet is operable to move between an open and closed position under the influence of a pressure differential. In an open position, the leaflet allows blood to flow through the valve. In a closed portion, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer can be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to any material with biocompatible characteristics including synthetic, such as, but not limited to, a biocompatible polymer, or a biological material, such as, but not limited to, bovine pericardium. Biocompatible material may comprise a first film and a second film as described herein for various embodiments.

The terms native valve orifice and tissue orifice refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a valve.

As used herein, "couple" means to join, couple, connect, attach, adhere, affix, or bond, whether directly or indirectly, and whether permanently or temporarily.

Embodiments herein include various apparatus, systems, and methods for a prosthetic valve, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

In accordance with embodiments, the valve has leaflets that are supported by a leaflet frame that is coaxial with and at least partially nested within a body frame. Each of the body frame and leaflet frame may have different physical properties suitable for a particular purpose. In accordance with embodiments, the body frame may be relatively stiff so as to abut and fixedly engage the tissue orifice as well as provide dimensional stability to the valve. The leaflet frame may be relatively less stiff relative to the body frame. The benefit of the leaflet frame being relatively less stiff relative to the body frame may be to slow down the rate of loading on the leaflets to reduce the stress levels on the leaflets whereby improving valve durability. Stiff and stiffness, as used herein and as is commonly used in engineering, is a measure of the resistance to deformation given by a body. Stiff and stiffness is a function of, among other things, material properties, the shape of the object, and the boundary conditions on the object. Stiffness of the leaflet frame 130 (see FIG. 1A) may be measured by any number of methods known in the art. In accordance with one method, cables may be coupled to each of the three posts 131 and brought together so as to allow the cables to be pulled simultaneously along the axis of the leaflet frame, with the leaflet frame restrained about the flex points 136 or as held by the body frame 120. The amount of force on the cables required to deflect the three posts toward the axis provides a measure of stiffness. The same may be done with the body frame 120 with the cables coupled to three equally spaced points on the body frame 120, such as an apex of the diamond-shaped apertures 122 opposite from the flex points 136.

The Valve

Figure 1B:
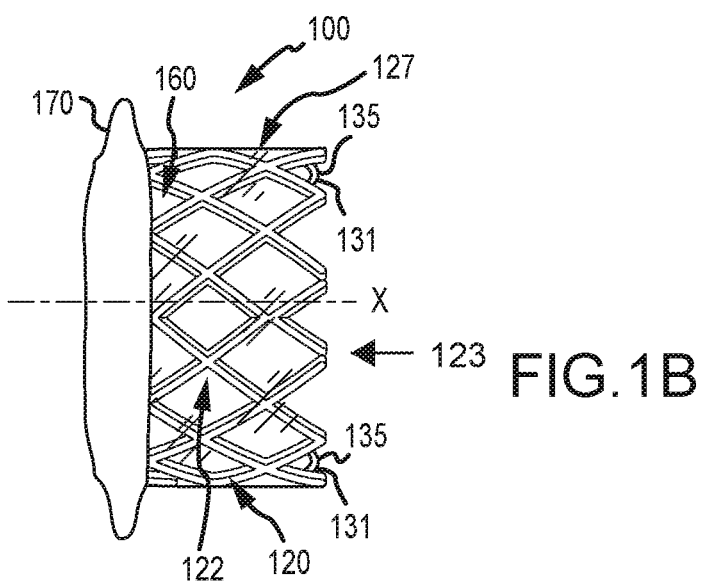
FIG. 1B is a side view of the embodiment of the valve of FIG. 1A.
Figure 1C:
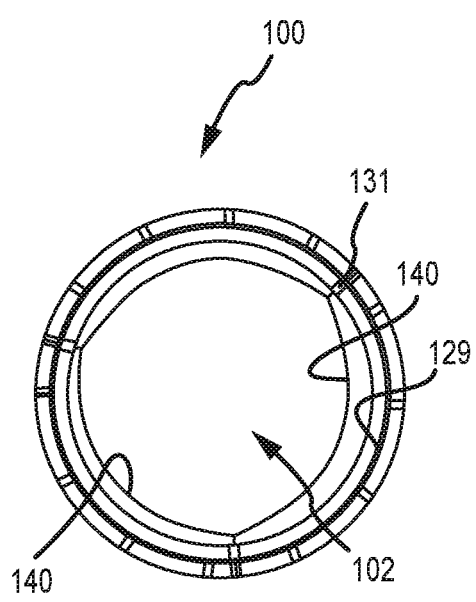
FIG. 1C is an axial view of the embodiment of the valve of FIG. 1A in an open configuration.
Figure 1D:
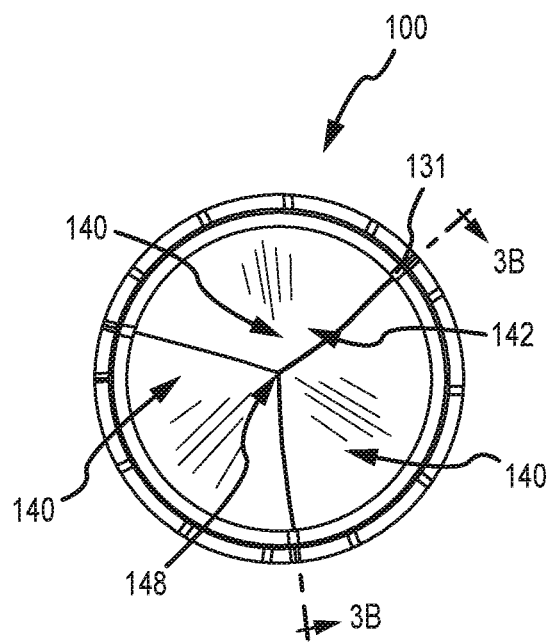
FIG. 1D is an axial view of the embodiment of the valve of FIG. 1A in a closed configuration.
Figure 2A:
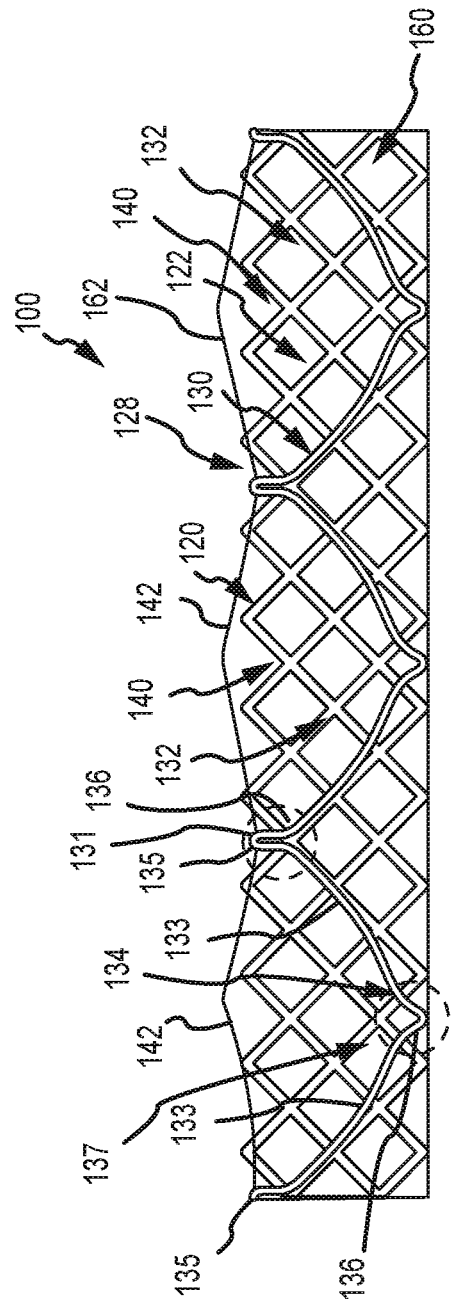
FIG. 2A is a representation of the embodiment of the valve of FIG. 1A unrolled to a flat orientation.
Figure 2B:
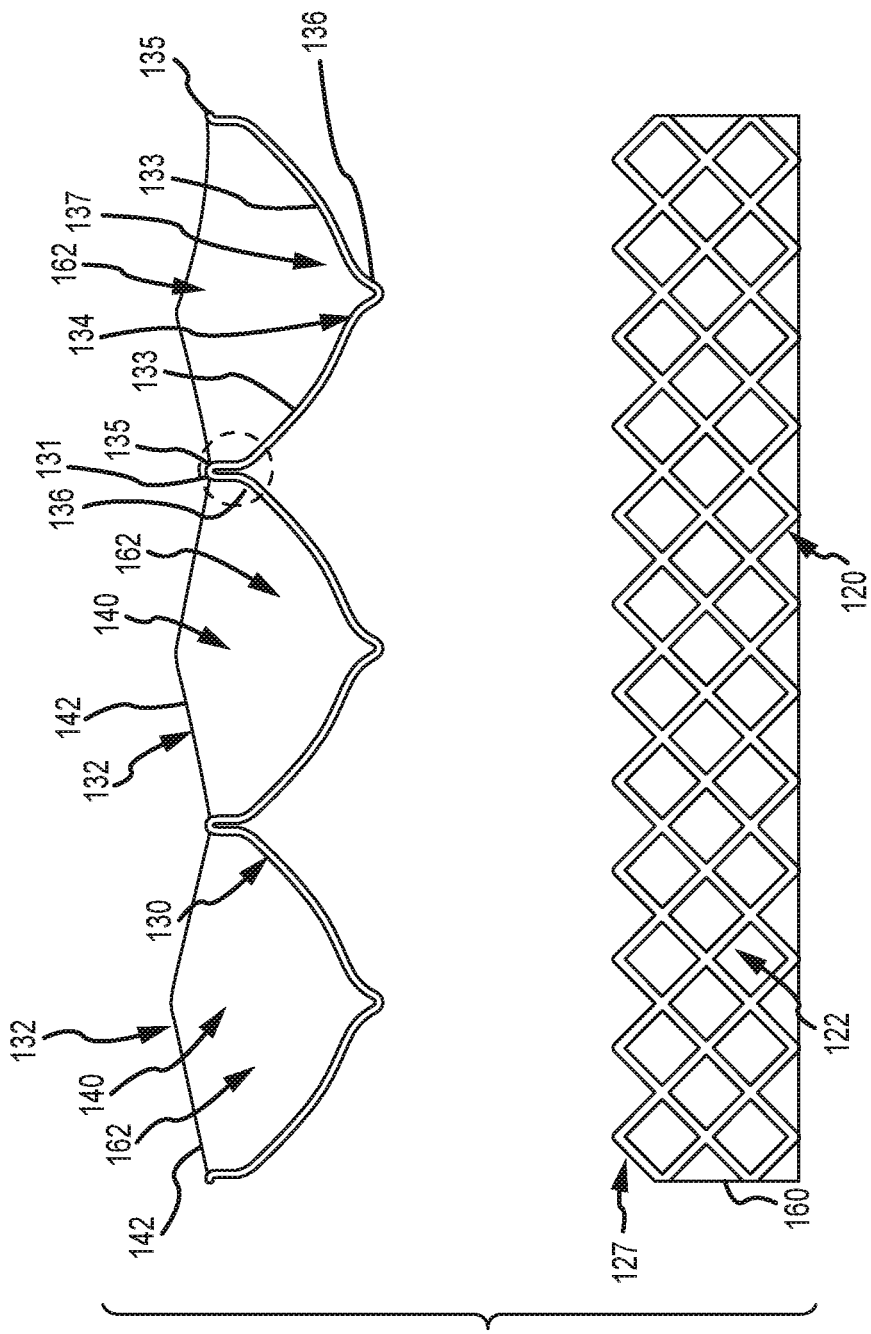
FIG. 2B is an exploded view of a representation of the embodiment of the valve of FIG. 1A unrolled to a flat orientation.

FIGS. 1A and 1B are perspective and side views, respectively, of a valve 100, in accordance with an embodiment. FIGS. 1C and 1D are axial views of the valve 100 in an open and closed configuration, respectively. FIG. 2A illustrates the embodiment of FIG. 1A wherein the valve 100 has been longitudinally cut and laid open to better illustrate the elements of the generally tubular-shaped valve 100. FIG. 2B illustrates the embodiment of FIG. 1A wherein the valve 100 has been longitudinally cut and laid open, and partially exploded so as to better illustrate the elements of the generally tubular-shaped valve 100.

The valve 100 comprises a body frame 120, a leaflet frame 130, and a first film 160 covering the body frame 120 and a second film 162 covering the leaflet frame 130 and forming leaflets 140.

The Film

A film 160 is generally any sheet-like, biocompatible material configured to couple to the body frame 120 and the leaflet frame 130. The leaflets 140 can also be comprised of the film 160. In an embodiment, the film 160 can be formed from a generally tubular material to couple the body frame 120 and the leaflet frame 130, and to form the leaflets 140.

It is understood that the film 160 is used generically for one or more biocompatible materials suitable for a particular purpose. It is also understood that the film coupled to the body frame 120 may not be the same film coupled to the leaflet frame 130, or the same film serving as leaflets 140, although in some embodiments the same film is coupled to the body frame 120 and the leaflet frame 130 and defines leaflets 140.

The film 160 can comprise one or more of the membrane, composite material, or laminate. Details of various types of film 160 are discussed below.

The Body Frame

The body frame 120 is a generally tubular member defining a body frame lumen 123 having a body frame inner surface 129, as shown in FIGS. 1A, 1B. The body frame 120 defines a valve orifice 102. The body frame 120 provides structural, load-bearing support to the leaflet frame 130. In addition, the body frame 120 can be configured to provide positive engagement to the recipient tissue at the implantation site.

The body frame 120 can comprise any metallic or polymeric material that is generally biocompatible. For example, the body frame 120 can comprise a material, such as, but not limited to nitinol, cobalt-nickel alloy, stainless steel, and polypropylene, acetyl homopolymer, acetyl copolymer, ePTFE, other alloys or polymers, or any other biocompatible material having adequate physical and mechanical properties to function as described herein.

By way of example, and as illustrated in the embodiments of FIGS. 1A-1D and 2A-2B, the valve 100 includes the body frame 120 that defines a stent having apertures 122. The open framework of the stent can define any number of features, repeatable or otherwise, such as geometric shapes and/or linear or meandering series of sinusoids. An open framework can be etched, cut, laser cut, or stamped into a tube or a sheet of material, with the sheet then formed into a substantially cylindrical structure. In other embodiments, the body frame 120 can have a solid wall. Alternatively, an elongated material, such as a wire, bendable strip, or a series thereof, can be bent or braided and formed into a substantially cylindrical structure. For example, body frame 120 can comprise a stent or stent graft type structure or a conventional sewing frame.

In accordance with embodiments, the body frame 120 can be configured to provide positive engagement to an implant site. In an embodiment, the valve 100 further includes a sewing cuff 170 coupled about the body frame 120, as shown in FIG. 1B, that is operable to accept suture so as to be sewn to a tissue orifice 150, for example, to maintain position, as shown in FIG. 4. In another embodiment, the body frame 120 can comprise one or more anchors (not shown) configured to engage the implant site, such as the tissue orifice 150 to secure the valve 100. In other embodiments, the body frame 120 can be otherwise secured to the implant site. It is understood that conventional, surgical techniques to implant prosthetic valves can be used to implant the valve 100, in accordance with embodiments. It is understood that valves in accordance with some embodiments may be implanted using intravascular techniques.

It is appreciated that other elements or means for coupling the valve 100 to an implant site are anticipated. By way of example, but not limited thereto, other means, such as mechanical and adhesive means may be used to couple the valve 100 to a synthetic or biological conduit.

Leaflet Frame

The leaflet frame 130 comprises a generally annular member defining a predetermined repeating pattern as shown in FIGS. 1A and 2A-2B. The leaflet frame 130 can comprise a wire, ribbon, cut tube, or any other element suitable for the particular purpose. As shown in FIGS. 2A-2B, the leaflet frame 130 comprises three interconnected U-shaped portions 132. Each of the U-shaped portions 132 defines two sides 133 that define a base 134, with each side 133 having a free end 135. In this embodiment, the base 134 defines a flex point 136 which will be described further below. The free end 135 of one U-shaped portion 132 is interconnected with a free end 135 of an adjacent U-shaped portion 132 which define a post 131.

A relatively less stiff leaflet frame 130 supporting the leaflets 140 can be more likely to reduce the loading encountered by the opening and closing leaflets 140 as compared to a more stiff leaflet frame 130. The leaflet frame 130 having a relatively less stiff property may reduce leaflet accelerations and reduce the closing stresses on the leaflets 140. In addition, the leaflet frame 130 can be elastically deformable so as to allow the leaflet frame 130 to flex and thus to facilitate surgical placement.

The leaflet frame 130 can comprise, such as, but not limited to, any elastically deformable metallic or polymeric material that is generally biocompatible. The leaflet frame 130 can comprise a shape-memory material, such as nitinol, a nickel-titanium alloy. Other materials suitable for the leaflet frame 130 include, but not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a leaflet frame 130 as described herein.

In accordance with an embodiment, the leaflet frame 130 comprises a shape memory material operable to flex under load and retain its original shape when the load is removed. The leaflet frame 130 and the body frame 120 can comprise the same or different materials.

Leaflet

Each of the U-shaped portions 132 of the leaflet frame 130 defines an inner region 137. Each inner region 137 is provided with a biocompatible material, such as the second film 162 which can be coupled to the sides 133 and base 134 of the leaflet frame 130; wherein the second film 162 defines a leaflet 140. Each leaflet 140 defines a leaflet free edge 142.

In accordance with an embodiment, the leaflet 140 can comprise a biocompatible material that is not of a biological source and that is sufficiently compliant and strong for the particular purpose, such as a biocompatible polymer. In an embodiment, the leaflet 140 comprises a membrane that is combined with an elastomer to form a composite material. In accordance with other embodiments, the biocompatible material that makes up the leaflet 140 comprises a biological material, such as, but not limited to, bovine pericardium.

The shape of the leaflets 140 are defined in part by the shape of the leaflet frame 130 and the leaflet free edge 142. The shape of the leaflets 140 can also be defined by the structures and processes used to manufacture the valve 100, such as, but not limited, those described below. For example, in accordance with an embodiment, the shape of the leaflets 140 also depends in part on molding the leaflets 140 using molding and trimming processes to impart a predetermined shape to the leaflet 140.

In an embodiment, substantially the entire leaflet frame 130 lies adjacent to the body frame inner surface 129. As such, when the leaflets 140 are in a fully open position, the valve 100 presents a substantially circular valve orifice 102 as shown in FIG. 1C, where the leaflet frame 130 minimally extends into the valve orifice 102. Fluid flow is permitted through the valve orifice 102 when the leaflets 140 are in an open position.

The leaflets 140 generally flex about the base 134 of the U-shaped portion 132 as the leaflets 140 open and close. In an embodiment, when the valve 100 is closed, generally about half of each leaflet free edge 142 abuts an adjacent half of a leaflet free edge 142 of an adjacent leaflet 140, as shown in FIG. 1D. The three leaflets 140 of the embodiment of FIG. 1D meet at a triple point 148. The valve orifice 102 is occluded when the leaflets 140 are in the closed position stopping fluid flow.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 can comprise any number of U-shaped portions 132, and thus leaflets 140, suitable for a particular purpose. Leaflet frames 130 comprising one, two, three or more U-shaped portions 132 and corresponding leaflets 140 are contemplated.

Valve Film

As shown in FIG. 1A, the body frame 120 is located coaxially about the leaflet frame 130 and, as shown in FIG. 2A, layered therewith in the unwrapped view of the valve 100. The valve 100 can comprise a film that couples at least a portion of the leaflet frame 130 to the body frame 120.

It is contemplated that the film 160 can be coupled to the leaflet frame 130 and the body frame 120 in many ways suitable for a particular purpose. By way of example, and not limited thereto, the body frame 120 can be wrapped with overlapping layers of a first film 161 having a first composition. The leaflet frame 130 can be wrapped with overlapping layers of a second film 162 having a second composition.

The film 160 can be coupled to the inside or outside surface of the leaflet frame 130 and body frame 120. In an embodiment, the film 160 can be coupled to both the inside and outside surfaces of both the leaflet frame 130 and the body frame 120. In another embodiment, the film 160 can be coupled to the inside surface of the leaflet frame 130 and the outside surface of the body frame 120 sandwiching at least a portion of the leaflet frame 130 and body frame 120 between the film 160, or vise versa, such that the leaflet frame 130 and body frame 120 are coupled together by the film 160.

The film 160 can be configured to prevent blood from traveling through or across the valve 100 other than through the valve orifice 102 when the leaflets 140 are in an open position. As such, the film 160 creates a barrier to blood flow in any interstitial space(s) of the body frame 120 and leaflet frame 130, and therebetween, that the film 160 covers.

The film 160 is fixedly secured or otherwise coupled at a single or a plurality of locations of the inside or outside surface of the body frame 120 and leaflet frame 130, for example, using one or more of taping, heat shrinking, adhesion and other processes known in the art. In some embodiments, a plurality of membrane/composite layers, i.e., a laminate, are used and can be coupled to the body frame 120 and the leaflet frame 130 to form at least a portion of the film 160.

The film 160 comprises any material(s) that have the suitable physical and mechanical properties to perform the functions described herein. A first film 161 coupled to the body frame 120 may comprise the same material that a second film 162 that the leaflet 140 comprises, as described above, or a different material. Similarly, the film 160 may or may not be homogenous in material composition. Different portions of the film 160 can comprise different materials which can give it predetermined physical and mechanical properties.

Leaflet Frame Engagement and Clasp

In accordance with an embodiment, any portion of the leaflet frame 130 that is not coupled to the body frame 120 by the film 160 can be in urging engagement against the body frame inner surface 129. In accordance with an embodiment, the leaflet frame 130 can have a spring bias wherein the leaflet frame 130 engages the body frame 120 in biased urging engagement.

In accordance with an embodiment, the posts 131 abut the inner surface 129 of the body frame 120, as shown in FIG. 1A. In accordance with yet another embodiment, the posts 131 are coupled with the body frame inner surface 129 by an engagement element (not shown) defined by the body frame 120.

In accordance with an embodiment, as shown in FIGS. 1A and 3A-3B, the posts 131 are positioned relative to the body frame 120 by the engagement of the posts 131 lying within a valley 128 defined by the body frame 120, as shown in FIG. 2A. The valley 128 can be operable to align the post 131 with the apex of the valley 128 so as to preferentially position the post 131 with respect to the body frame 120. It is understood that the posts 131 can lie entirely within the body frame 120, or at least partially extending from and outside of the body frame 120.

The engagement of the posts 131 of the leaflet frame 130 with the body frame 120 can provide support to the leaflet frame 130. The engagement of the posts 131 with the body frame 120 allows for the transfer of loading on the leaflet 140 to the leaflet frame 130 and then to the body frame 120. It is contemplated that the degree of engagement of the leaflet frame 130 with the body frame 120 will determine the degree of support provided on the leaflet frame 130 by the body frame 120, which can be predetermined for a particular purpose.

In other embodiments, a portion of the leaflet frame including a portion of the posts 131 is not coupled to the first film 160 and not held in engagement with the body frame inner surface 129 so as to allow inward flexing of the posts 131 under the loading of the leaflet 140 during valve operation, particularly when closing or closed. Flexing of the posts 131 can ensure that the leaflet free edges 142 coapt to form a tight seal when closed. In various embodiments, the degree of inward flexing of the posts 131 during valve operation will determine the degree of coaptation, which can be predetermined for a particular purpose.

In accordance with an embodiment, one or more clasps (not shown) or some other similar engagement mechanism can secure the post 131 to the body frame 120 and add a predetermined amount of structural rigidity to the leaflet frame 130. As such, loading on the leaflet frame 130 can at least partially be transferred or distributed to the body frame 120. In this regard, the clasp comprises any structure configured to interlock, connect, fasten, or otherwise hold the leaflet frame 130 and body frame 120 together. The clasp connecting the leaflet frame 130 to the body frame 120 is operable to transfer at least some of the load on the leaflet frame 130 to the body frame 120.

Body Frame and Leaflet Frame Compared

In embodiments of the valve 100, the inclusion of a body frame 120 and a leaflet frame 130 provides a means for providing different physical properties for each of the body frame 120 and the leaflet frame 130 suitable for a particular purpose. In accordance with an embodiment, the body frame 120 is less stiff as compared with the leaflet frame 130. The body frame 120, when engaged to the implant site, such as, but not limited to the tissue orifice 150 as shown in FIG. 4, is rigid enough to not significantly recoil to a smaller diameter or deform under physiological loading.

The physical properties of the body frame 120 and the leaflet frame 130 depends, in part, on the size, shape, thickness, material property of the body frame 120 and the leaflet frame 130 as well as the different physical properties and number of layers or wrappings of the film 160 as well as the coupling of the body frame 120 and the leaflet frame 130.

Film

The second film 162 that makes up the leaflet 140 can comprise any biocompatible material sufficiently compliant and flexible, such as a biocompatible polymer. The second film 162 can comprise a membrane that is combined with an elastomer to form a composite material. The second film 162, according to an embodiment, includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore, in accordance with an embodiment. The fibrils extend from the nodes in a plurality of directions, and the membrane has a generally homogeneous structure. Membranes having this microstructure can typically exhibit a ratio of matrix tensile strength in two orthogonal directions of less than 2, and possibly less than 1.5. Embodiments of expanded fluoropolymer membrane provided herein contain a majority of fibrils having a diameter that is less than about 1 μm. Other embodiments of expanded fluoropolymer membrane provided herein contain a majority of fibrils having a diameter that is less than 0.1 μm. The embodiments provided herein recognize that a membrane comprising fibrils the majority of which are less than about 1 to beyond less than about 0.1 μm provide a significant improvement to, at least, but not limited to, the durability and lifetime of the heart valve when used as leaflet material. Embodiments of expanded fluoropolymer membrane provided herein may have a mean flow pore sizes of less than about 5 μm, less than about 1 μm, and less than about 0.10 μm, in accordance with embodiments.

In another embodiment, the expanded fluoropolymer membrane has a microstructure of substantially only fibrils, such as, for example, as is generally taught by U.S. Pat. No. 7,306,729, to Bacino in accordance with an embodiment. The expanded fluoropolymer membrane having substantially only fibrils can possess a high surface area, such as greater than 20 m$^2$/g, or greater than 25 m$^2$/g, and in some embodiments can provide a highly balanced strength material having a product of matrix tensile strengths in two orthogonal directions of at least 1.5×10$^5$ MPa$^2$, and/or a ratio of matrix tensile strengths in two orthogonal directions of less than 4, and possibly less than 1.5. Embodiments of expanded fluoropolymer membrane provided herein contain a majority of fibrils having a diameter that is less than about 1 μm. Other embodiments of expanded fluoropolymer membrane provided herein contain a majority of fibrils having a diameter that is less than about 0.1 μm. The embodiments provided herein recognize that a membrane comprising fibrils the majority of which are less than about 1 to beyond less than about 0.1 μm provide a significant improvement to, at least, but not limited to, the durability and lifetime of the heart valve when used as leaflet material. Embodiments of expanded fluoropolymer membrane provided herein may have a mean flow pore sizes of less than about 5 μm, less than about 1 μm, and less than about 0.10 μm, in accordance with embodiments.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 µm. The expanded fluoropolymer membrane can possess a mass per area of about 1.15 g/m². Membranes according to an embodiment of the invention can have matrix tensile strengths of about 411 MPa in the longitudinal direction and 315 MPa in the transverse direction.

Additional materials can be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 µm and a mass per area of about 4.1 g/m².

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet 140 by eliminating or reducing the stiffening observed with ePTFE-only materials. In addition, it can reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment, the elastomer is present in substantially all of the pores of the at least one fluoropolymer layer. Having elastomer filling the pore volume or present in substantially all of the pores reduces the space in which foreign materials can be undesirably incorporated into the composite material. An example of such foreign material is calcium that can be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. hereby incorporated by reference in its entirety. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In another embodiment, the ePTFE comprises pores with the elastomer present in substantially all of the pores. The composite material comprises less than about 80% ePTFE by weight in the range of about 10% to 90%.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang hereby incorporated by reference in its entirety.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Sewing Cuff

The valve 100 further comprises a sewing cuff 170 about a body frame outer surface 127 in accordance with an embodiment, as shown in FIG. 1B; not shown in FIG. 1A for clarity. The sewing cuff 170 is operable to provide structure that receives suture for coupling to the implant site. The sewing cuff 170 may comprise any suitable material, such as, but not limited to, double velour polyester. The sewing cuff 170 may be located circumferentially around the base frame 120 or perivalvular depending from the base frame 120.

Other Considerations

In accordance with an embodiment, the valve 100 can be configured to prevent interference with a heart conduction system by not covering a bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the functional diameter. However, the valve 100 can be constructed at any length and, more generally, any desirable dimension.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents, such as, but not limited to, heparin. Other bio-active agents can also include, but are not limited to agents such as, but not limited to, antiproliferative/antimitotic agents including natural products such as *vinca* alkaloids (i.e. vinblastine, vincristine, and vinorelbine), paclitaxel, epipidophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Method of Making

Figure 5:
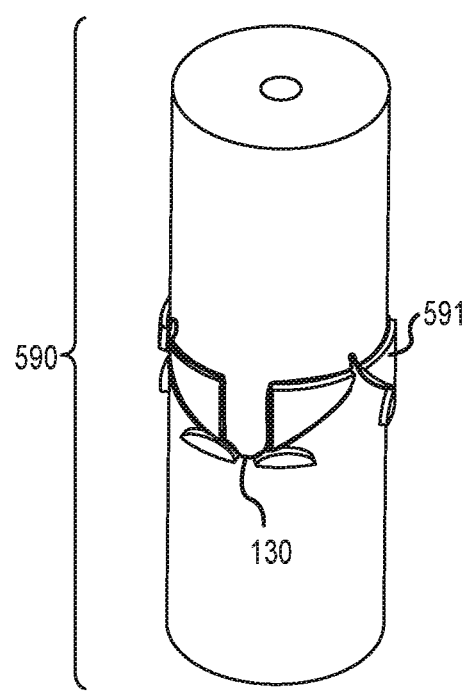
FIG. 5 is a perspective view of an embodiment of a winding jig for forming a wire into a leaflet frame.

Embodiments described herein also pertain to a method of making the valve embodiments as described herein. In order to make the various embodiments, a winding jig and a two-piece leaflet mandrel can be used. With reference to FIG. 5, winding jig 590 comprises a structural form defining the valve orifice of the valve and a leaflet frame guide 591 configured to facilitate the shaping of a wire into a desired shape of the leaflet frame 130.

With reference to FIG. 5, a method of making the leaflet frame 130 can comprise the step of shaping a wire to form leaflet frame 130. Winding jig 590 can be used to form the leaflet frame 130 wherein wire is bent around posts and guides and then heat set. The ends of the wire are coupled together.

Figure 6A:
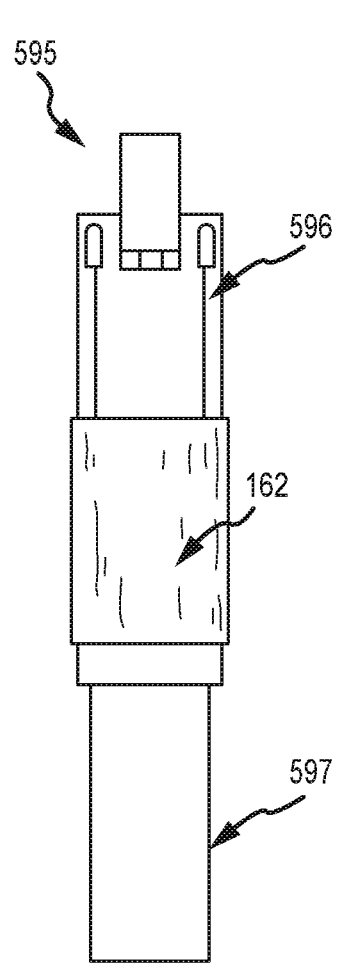
Figure 6B:
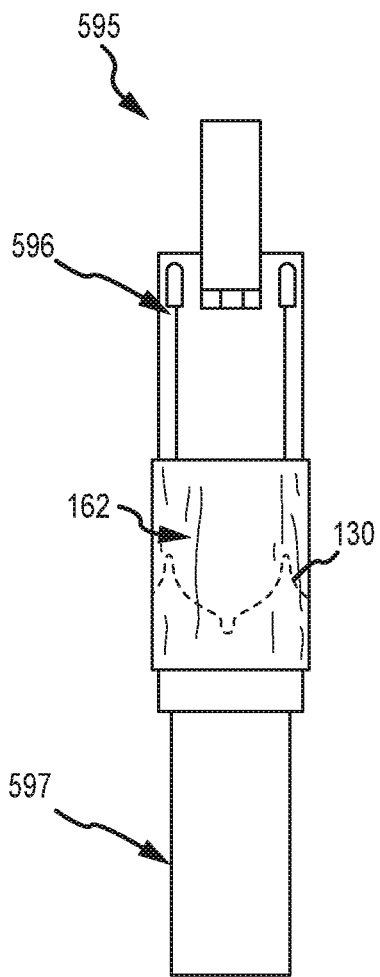
Figure 6H:
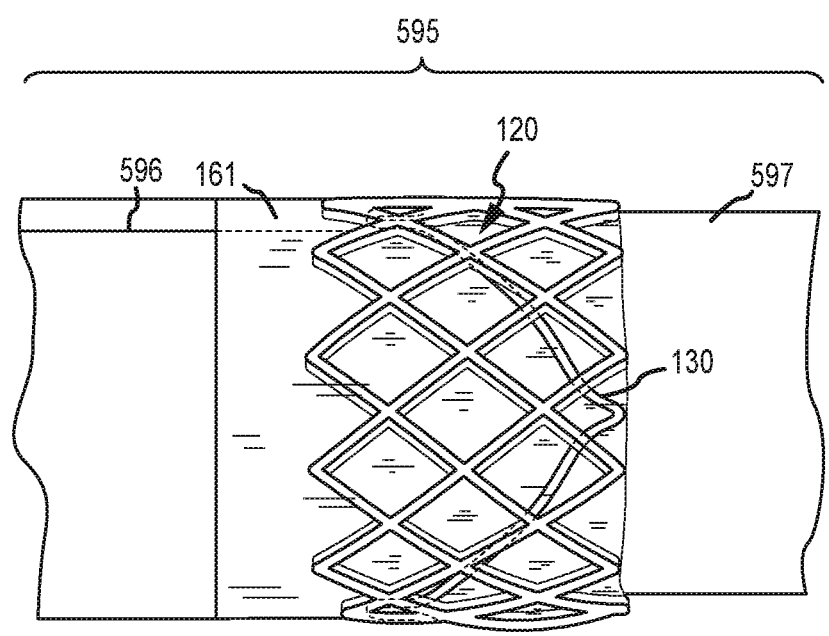

With reference to FIGS. 6A-6H, an embodiment of a method of making valve 100 comprises the steps of wrapping a first layer of second film 162, e.g., a composite as described herein, into a tubular form about a two-piece mandrel 597, as shown in FIG. 6A; placing the leaflet frame 130 over the first layer of second film 162; forming a second layer of second film 162 over the leaflet frame 130, as shown in FIG. 6B, placing a leaflet clamp 596 in urging engagement with the second film 162 about the U-shaped portions 132 of the leaflet frame 130 that will become the leaflets 140, as shown in FIG. 6C; molding the leaflets 140 with the leaflet clamp 596, as shown in FIG. 6D-6E; forming a third layer comprising a first film 161 over the leaflet frame 130, as shown in FIG. 6F; placing the body frame 120 about the third layer and the leaflet frame 130, as shown in FIG. 6G; wrapping a fourth layer comprising the first film 161 over the body frame 120, as shown in FIG. 6H; and thermally setting the assembly.

With reference to FIG. 6E, a two-piece mandrel 595 comprises a leaflet clamp 596 and a base mold 597 which together form the mandrel to mold a tubular membrane or composite to form the leaflets 140. Leaflet clamp 596 can comprise contoured grooves 594 along the seams of the leaflet clamp 596 wherein the posts 131 will be placed into in order to facilitate the desired spring bias or inward flexing in the leaflet frame 130.

EXAMPLE

By way of example, one embodiment of a valve was made as follows:

A leaflet frame was constructed by winding a nitinol wire (0.020" diameter) onto a winding jig as illustrated in FIG. 5. Once the pattern as shown in FIG. 2B was obtained, the frame was shape set in an oven set to 450° C. for 10 minutes. The two ends of the wire were coupled together. The leaflet frame was then exposed to a surface roughening step to improve adherence of the second film 162 to the leaflet frame. The leaflet frame was submersed in an ultrasonic bath of acetone for approximately five minutes. The leaflet frame surface was then subjected to a plasma treatment with methods commonly known to those having ordinary skill in the art.

FEP powder (Daikin America, Orangeburg N.Y.) was applied to the leaflet frame. The leaflet frame was then heated in a forced air oven set to 320° C. for approximately three minutes. In this way, the powder was melted and adhered as a thin coating to the entire frame. The leaflet frame was removed from the oven and left to cool to room temperature.

A body frame was laser cut from a tube of 316 stainless steel having a wall thickness of about 0.5 mm (0.02"), a diameter of about 2.5 cm (1.0"), and a length of 2 cm. A diamond-shaped pattern was cut into the tube to form an annular-shaped body frame as shown in FIG. 2B. The same surface treatment and FEP powder coating steps as described above were applied to the body frame.

A second film 162 was obtained. A membrane of ePTFE can be manufactured according to the general teachings described in U.S. Pat. No. 7,306,729 to Bacino et al. The ePTFE membrane can have a mass per area of 1.15 g/m$^2$, a bubble point of 79.7 MPa, a thickness of about 1.016 µm, a matrix tensile strength of 410.9 MPa in the longitudinal direction and 315.4 MPa in the transverse direction. The ePTFE membrane was imbibed with a fluoroelastomer to form a composite material.

A fluoroelastomer that is a copolymer comprising tetrafluoroethylene and perfluoro(methyl vinylether) as described in U.S. Pat. No. 7,462,675 to Chang, et al. was obtained. The copolymer consists essentially of between about 65 and 70 weight percent perfluoromethyl vinyl ether and complementally about 35 and 30 weight percent tetrafluoroethylene.

This copolymer was dissolved in Novec HFE7500 (3M, St Paul, MN) in a 2.5% concentration. The ePTFE membrane (while being supported by a polypropylene release film) was coated with the prepared solution using a mayer bar and dried in a convection oven set to 145° C. for 30 seconds thereby creating an imbibed composite material. After the two coating steps, the final ePTFE/fluoroelastomer or composite material had a mass per area of approximately 4.08 g/m$^2$, 28.22% fluoropolymer by weight, a dome burst strength of 15.9 KPa, and a thickness of 1.89 μm.

Fifteen layers of the composite material, the second film 162, were wrapped around the combined 25 mm diameter aluminum mandrel assembly shown in FIG. 6A with the elastomer rich side facing away from the mandrel. The layers of composite material were each circumferentially wrapped around the mandrel so as to orient the transverse direction of the composite along the longitudinal axis of the mandrel. Each additional layer wrapped around the mandrel assembly was oriented in the same fashion.

The leaflet frame was everted from its wire wound condition, then coaxially positioned on the mandrel, as illustrated in FIG. 6B.

A second layer of the second film 162 comprising five additional layers of membrane material were wrapped around the combined mandrel assembly and over the leaflet frame with the elastomer rich side facing toward the leaflet frame The leaflets were then formed to a predetermined shape by positioning the leaflet clamp 596 as shown in FIG. 6C-6E and subsequently closing the leaflet clamp 596 against the second film 162 about the about the U-shaped portions 132 of the leaflet frame 130 that subsequently became the leaflets 140.

A first layer comprising first film 161 comprising five layers of membrane material were wrapped around the combined mandrel assembly with the elastomer rich side facing outward, as shown in FIG. 6F. The body frame was then positioned onto the mandrel in operable relationship to the leaflet frame, as shown in FIG. 6G. A second layer comprising the first film 161 comprising five additional layers of composite material were wrapped around the body frame with the elastomer rich side of each layer facing toward the body frame, as shown in FIG. 6G.

The combined mandrel assembly was then thermal treated to set the leaflet shape and to consolidate the biocompatible material. The first film 161 and second film 162 were trimmed in accordance with the configuration as shown in FIGS. 1A-2B.

Testing Methods

It should be understood that although certain methods and equipment are described below, any method or equipment determined suitable by one of ordinary skill in the art may be alternatively utilized.

Bubble Point and Mean Flow Pore Size

Bubble point and mean flow pore size were measured according to the general teachings of ASTM F31 6-03 using a capillary flow Porometer, Model CFP 1500AEXL from Porous Materials, Inc., Ithaca NY, USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. The test fluid was isopropyl alcohol. Using the Capwin software version 7.73.012 the following parameters were set as specified in the table below. As used herein, mean flow pore size and pore size are used interchangeably.

| Parameter | Set Point |
| --- | --- |
| (cm$^3$/m) | 200000 |
| Bublflow (cm$^3$/m) | 100 |
| F/PT (old bubltime) | 50 |
| Minbpress (PSI) | 0 |
| Zerotime (sec) | 1 |
| V2incr (cts) | 10 |
| Preginc (cts) | 1 |
| Pulse delay (sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm$^3$/m) | 500 |

Presence of Elastomer within the Pores

The presence of elastomer within the pores can be determined by several methods known to those having ordinary skill in the art, such as surface and/or cross section visual, or other analyses. These analyses can be performed prior to and after the removal of elastomer from the composite.

Diameter of Fibrils

The average diameter of the fibrils was estimated by examining micrographs that were obtained having at a magnification suitable for showing numerous fibrils. In the case of a composite material, it may be necessary to extract the elastomer or other material that may be filling the pores, by any suitable means, to expose the fibrils.

Mass, Thickness, and Density of ePTFE Membranes

Membrane thickness was measured by placing the membrane between the two plates of a Kafer FZ1000/30 thickness snap gauge Kafer Messuhrenfabrik GmbH, Villingen-Schwenningen, Germany. The average of the three measurements was reported.

Membrane samples were die cut to form rectangular sections about 2.54 cm by about 15.24 cm to measure the weight (using a Mettler-Toledo analytical balance model AG204) and thickness (using a Kafer Fz1000/30 snap gauge). Using these data, density was calculated with the following formula: $\rho = m/(w*l*t)$, in which: $\rho$=density (g/cm$^3$), m=mass (g), w=width (cm), l=length (cm), and t=thickness (cm). The average of three measurements was reported.

Matrix Tensile Strength (MTS) of ePTFE Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm³.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A valve comprising:
 a body frame formed into a cylindrical structure having a body frame inner surface defining a body frame lumen;
 a leaflet frame that is coaxial with and nested within the body frame and includes a plurality of posts, wherein at least a portion of the leaflet frame is not held in engagement with the body frame inner surface such that the plurality of posts are operable to flex under loading during valve operation, the leaflet frame further including a plurality of U-shaped portions, each adjacent pair of the plurality of U-shaped portions being connected at one of the plurality of posts; and
 a plurality of leaflets supported by the plurality of posts of the leaflet frame, each of the plurality of leaflets having a U-shaped base that follows a U-shaped portion of one of the plurality of U-shaped portions of the leaflet frame.

2. The valve of claim 1, wherein;
 the plurality of posts are disposed entirely between axial inflow and outflow ends of the body frame; and
 the portion of the leaflet frame not held in engagement with the body frame includes at least a portion of the plurality of posts.

3. The valve of claim 1, wherein the plurality of posts at least partially extend beyond an axial outflow end of the body frame.

4. The valve of claim 1, further comprising a film positioned between the leaflet frame and the body frame, wherein the at least a portion of the leaflet frame is not coupled to the film positioned between the leaflet frame and the body frame.

5. The valve of claim 1, wherein the body frame and the leaflet frame have different stiffnesses.

6. The valve of claim 1, wherein:
 an outflow end of the body frame forms a plurality of valleys around a circumference of the body frame; and
 each of the plurality of posts of the leaflet frame is aligned with an apex of a respective one of the plurality of valleys of the body frame.

7. A valve comprising:
 a body frame formed into a cylindrical structure including a body frame inner surface defining a body frame lumen;
 a leaflet frame that is coaxial with and nested within the body frame such that the leaflet frame is positioned within the body frame lumen, the leaflet frame including a plurality of posts partially engaging the body frame, wherein:
  each of the plurality of posts includes an end that is free from the body frame; and
  a majority of each of the plurality of posts is disposed between axial inflow and outflow ends of the body frame; and
 a plurality of leaflets supported by the plurality of posts of the leaflet frame.

8. The valve of claim 7, wherein engagement of the plurality of posts of the leaflet frame with the body frame provides support to the leaflet frame and allows for transfer of loading on the plurality of leaflets to the leaflet frame and to the body frame.

9. The valve of claim 7, wherein the body frame and the leaflet frame have different stiffnesses.

10. The valve of claim 7, wherein each of the plurality of leaflets is coupled to the leaflet frame such that each leaflet has a U-shaped base.

11. A valve comprising:
 a multi-part frame defining a flow lumen through which fluid is able to selectively flow, the multi-part frame including:
  an outer frame having an annular form, the outer frame defining an outer frame lumen;
  a leaflet frame defining a plurality of commissure posts, each of the plurality of commissure posts include a free end, the leaflet frame being at least partially received within the outer frame lumen and fixedly coupled to the outer frame, wherein:
   the free end of each of the plurality of commissure posts is not held in engagement with the outer frame during valve operation and is operable to flex under loading during valve operation;
   the leaflet frame comprises a plurality of U-shaped portions; and
   each adjacent pair of the plurality of U-shaped portions is connected at one of the plurality of commissure posts; and
  a plurality of leaflets coupled to the leaflet frame, each leaflet having a U-shaped base that follows a U-shaped portion of one of the plurality of U-shaped portions of the leaflet frame, the plurality of leaflets being moveable between an open position and a closed position to selectively block and unblock the flow lumen.

12. The valve of claim 11, further comprising a cover material positioned between the leaflet frame and the outer frame.

13. The valve of claim 11, wherein the leaflet frame and the outer frame are configured to flex relative to one another during valve operation.

14. The valve of claim 11, wherein the outer frame and the leaflet frame have different stiffnesses.

15. The valve of claim 11, wherein the plurality of commissure posts are configured to flex inwardly and outwardly with respect to the outer frame during valve operation.

16. The valve of claim 11, wherein the multi-part frame is configured to permit flexing between the leaflet frame and the outer frame.

17. The valve of claim 11, wherein at least a majority of an axial dimension of the plurality of commissure posts is disposed between inflow and outflow ends of the outer frame.

18. The valve of claim 11, wherein:
an outflow end of the outer frame forms a plurality of valleys around a circumference of the outer frame; and
each of the plurality of commissure posts of the leaflet frame is aligned with an apex of a respective one of the plurality of valleys of the outer frame.

19. The valve of claim 7, wherein each of the plurality of posts of the leaflet frame is disposed entirely between the axial inflow and outflow ends of the body frame.

20. The valve of claim 7, wherein each of the plurality of posts of the leaflet frame extends beyond the axial outflow end of the body frame.

\* \* \* \* \*